United States Patent [19]

Hata et al.

[11] Patent Number: 5,302,587
[45] Date of Patent: Apr. 12, 1994

[54] PLATINUM (II) COMPLEX AND AGENT FOR TREATING MALIGNANT TUMOR

[75] Inventors: Go Hata, Fujisawa; Masato Mutoh, Yokohama; Hideyuki Hashimoto, Ohtsu, all of Japan

[73] Assignee: Toray Industries, Inc., Japan

[21] Appl. No.: 741,433

[22] PCT Filed: Dec. 11, 1990

[86] PCT No.: PCT/JP90/01610
§ 371 Date: Sep. 9, 1991
§ 102(e) Date: Sep. 9, 1991

[87] PCT Pub. No.: WO91/09041
PCT Pub. Date: Jun. 27, 1991

[30] Foreign Application Priority Data

Dec. 12, 1989 [JP] Japan .................. 1-323377

[51] Int. Cl.$^5$ .................. A61K 33/24; A61K 31/28; C07F 15/00
[52] U.S. Cl. .................. 514/184; 514/186; 549/3; 549/206; 549/210; 549/450; 549/451; 549/452
[58] Field of Search ............ 549/206, 3, 210; 514/184, 186; A61K 33/24

[56] References Cited

U.S. PATENT DOCUMENTS

| | | | |
|---|---|---|---|
| 4,783,452 | 11/1988 | Haines et al. | 549/206 |
| 4,912,100 | 3/1990 | Ohno | 549/210 |
| 4,980,347 | 12/1990 | Ohno | 549/210 |
| 5,011,959 | 4/1991 | Khokhar et al. | 549/206 |
| 5,034,552 | 7/1991 | Keppler et al. | 549/206 |

FOREIGN PATENT DOCUMENTS

| | | | |
|---|---|---|---|
| 222522 | 5/1987 | European Pat. Off. | 549/206 |
| 264109 | 4/1988 | European Pat. Off. | 549/206 |
| 46752 | 4/1979 | Japan . | |
| 2296 | 1/1982 | Japan . | |
| 97991 | 5/1985 | Japan . | |
| 209595 | 10/1985 | Japan . | |
| 63-112591 | 5/1988 | Japan | 549/206 |
| 6287 | 1/1989 | Japan . | |
| 1-163191 | 6/1989 | Japan | 549/206 |
| 246246 | 10/1989 | Japan . | |

OTHER PUBLICATIONS

Staquet et al, Cancer Treatment Reports vol. 67, No. 9, 1983, p. 753.

*Primary Examiner*—Cecilia Tsang
*Attorney, Agent, or Firm*—Austin R. Miller

[57] ABSTRACT

A novel platinum (II) complex represented by the following formula (A):

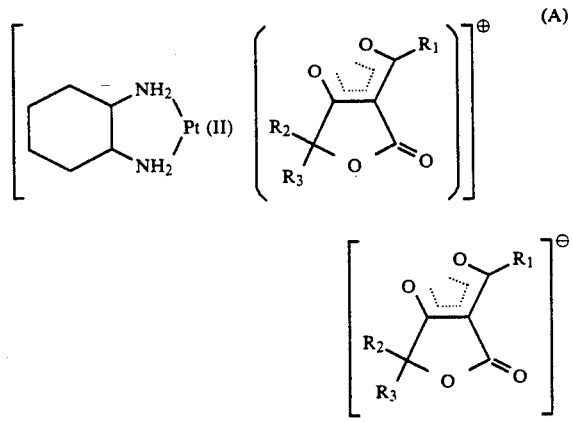

wherein $R_1$ represents $C_1$–$C_5$ lower hydrocarbon group, $R_2$ and $R_3$ represents hydrogen atom or $C_1$–$C_3$ lower hydrocarbon group, the configuration of 1,2-diaminocyclohexane being cis, trans-l- or trans-d-. Since the platinum (II) complex has a strong anti-tumor activity and its toxicity is low, it is useful as an agent for treating malignant tumor.

13 Claims, No Drawings

PLATINUM (II) COMPLEX AND AGENT FOR TREATING MALIGNANT TUMOR

TECHNICAL FIELD

The present invention relates to a novel platinum complex and to an agent for treating malignant tumor containing the same as an effective component.

BACKGROUND ART

A number of organic acid platinum (II) complexes wherein the ligand component is 1,2-diaminocyclohexane have been reported. However, many of them have low solubility so that they cannot be intravenously administered (e.g., cyclobutane-1,1-dicarboxylate disclosed in Japanese Laid Open Patent Application (Kokai) No. 60-10952) while the intravenous administration is the administration route of platinum complexes or, in the alternative, their stabilities in aqueous solutions are low although their solubilities are large (e.g., trimellitate disclosed by P. J. Andrulis et al., Proceedings of the Fifth International Symposium and Other Metal Compounds in Cancer Chemotherapy, p.450 (1987)).

On the other hand, there is a problem in seeking a platinum complex with anti-tumor activity that an impurity contaminated in the synthesized platinum complex often shows anti-tumor activity. Therefore, it is necessary to appropriately purify the platinum complex. Recently, James D. Hoeschele and N. Farrel reported examples wherein the anti-tumor activity of a platinum complex disappeared after an appropriate purification of the platinum complex in Inorg. Chem., 27, 4106–4113 (1988). That is, they reported that among the 1,2-diaminocyclohexane Pt(II) complexes which were reported to be water-soluble and to have high anti-tumor activities, some complexes lost their anti-tumor activities after purification. Thus, they emphasized the importance of obtaining a sample with a high purity for the evaluation of the anti-tumor activities.

The present inventors previously discovered that the platinum (II) complexes containing 1 mole of 1,2-diaminocyclohexane and 2 moles of 3-acetyl-6-methyl-tetrahydropyran-2,4-dione or its analogue have anti-tumor activities (EP 337,459). However, it turned out that these complexes do not show anti-tumor activities when they are highly purified. Thus, it is important for an industrial preparation that the synthesized complex can be purified easily and the complex with a high purity can be obtained easily.

The object of the present invention is to provide a novel platinum (II) complex with a strong anti-tumor activity, which may easily be purified, which has a solubility that enables intravenous administration, and which is stable in aqueous solution.

DISCLOSURE OF THE INVENTION

The present invention provides a novel platinum (II) complex represented by the following formula (A):

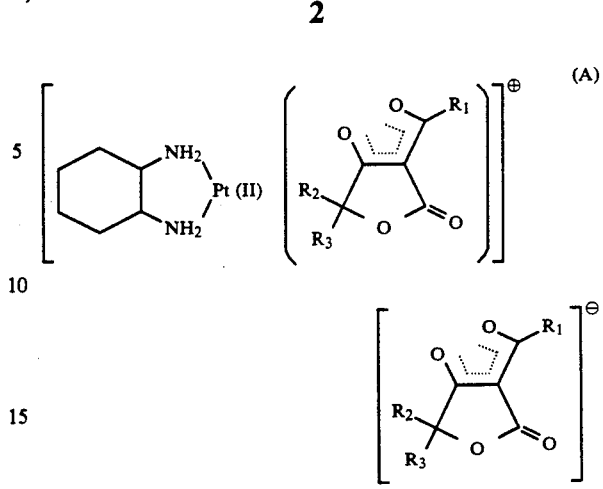

wherein $R_1$ represents $C_1-C_5$ lower hydrocarbon group, $R_2$ and $R_3$ represents hydrogen atom or $C_1-C_3$ lower hydrocarbon group, the configuration of 1,2-diaminocyclohexane being cis, trans-l- or trans-d- as well as an agent for treating malignant tumor comprising the complex as an effective component.

BEST MODE FOR CARRYING OUT THE INVENTION

The lower hydrocarbon group employed in the present invention is preferably alkyl group and alkenyl group such as methyl, ethyl, propyl, butyl, pentyl, vinyl, isopropyl, allyl and isopropenyl. Among these, methyl is especially preferred.

The moiety represented by the formula

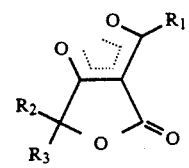

bonded to platinum in the complex of the formula (A) exhibits the tautomerism represented by the equation of

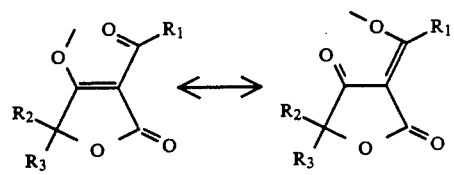

and chelates the platinum. The moiety

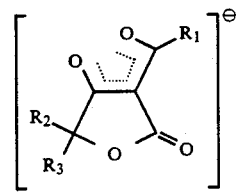

exhibits the tautomerism represented by the equation of

The present inventors discovered that a complex can be synthesized, in which one molecule of a deprotonated derivative of a five-membered ring compound (B) of the formula:

(B)

compound (B) exhibits the tautomerism presented by the equation of chelates the platinum (II) and another one molecule of the deprotonated derivative of the compound (B) in the form of an anion is attached thereto so as to form a complex. This complex is highly soluble in water and stable in aqueous solution, and has high anti-tumor activity.

The compound that may be synthesized is represented by the following equations (I) and (II).

(I)
Pt(OH)$_2$ + 2(B) ⟶ (A)
(C)

(II)
Pt(NO$_3$)$_2$ or PtSO$_4$ +
(D)         (E)

$$2(B) \xrightarrow{\text{alkaline metal hydroxide or}}_{\text{alkaline earth metal hydroxide}} (A)$$

The compound (C) may be obtained by passing the compound (D) through a strong ion-exchange resin.

The compound (D) and (E) which are the materials for synthesizing the platinum complex of the present invention may be obtained by known methods. For example, they may be obtained easily by treating the compound of the following formula (F) with silver nitrate or silver sulfate according to the procedure described in Journal of Pharmaceutical Sciences, 65, 315, (1976).

(F)

wherein Hal represents halogen

The compound (F) has three isomers, that is, Pt(cis-1,2-diaminocyclohexane)Hal$_2$, Pt(trans-l-1,2-diaminocyclohexane)Hal$_2$, and Pt(trans-d-1,2-diaminocyclohexane)Hal$_2$ depending on the configuration of the 1,2-diaminocyclohexane used.

As the alkaline metal hydroxide used in the reaction (II), NaOH and KOH are preferred and as the alkaline earth metal hydroxide used therein, Ba(OH)$_2$ and Ca(OH)$_2$ are preferred. Two equivalents of the alkaline metal hydroxide or one equivalent of the alkaline earth metal hydroxide may preferably be used.

The compound represented by the formula (B), which is another material, may be prepared by known methods, for example, by the method according to E. Benary, Berichte 42, 3912 (1909), or P. M. Booth et al., J. Chem. Soc. Perkin Trans, I, 121 (1987), or D. J. Agar et al., Tetrahedron Lett., 29, 4807 (1988).

Although the molar ratio of the compound (B) to the compounds (C), (D) and (E) may preferably be about 2, no problem is caused even if an excess amount of the compound (B) is used.

The fact that the two moles of the deprotonated derivatives of the compound (B) are not identical is apparent from the fact that the proton signals with the same intensity are separately observed in NMR. The fact that the complex forms an ionic compound is known from the fact that one mole of the deprotonated derivative of B in the complex is easily replaced by another ion such as an acetate ion. The complex of the present invention may be in the form of an aquocomplex containing water and the aquocomplex is also included in the scope of the present invention.

The present inventors previously found that the platinum (II) complexes containing 1 mole of 1,2-diaminocyclohexane and 2 moles of 3-acetyl-6-methyltetrahydropyrane-2,4-dione or its analogue have anti-tumor activities. However, it turned out that these complexes do not show anti-tumor activities when they are purified by using liquid column chromatography (column: styrene-divinylbenzene copolymer), as shown in the reference examples hereinbelow described.

The complex of the present invention may be purified by liquid column chromatography and/or recrystallization. If the complex is composed of an optically single compound, it can easily be purified by recrystallization. Water is preferably used as the solvent for recrystallization.

The toxicity of the complex of the present invention is low since the ratio of (LD$_{50}$ value)/(minimum dose exhibiting anti-tumor activity) is large.

The agent containing an effective amount of the platinum complex of the present invention may be clinically administered orally or parenterally. The agent may be in the form of a tablet, sugar-coated tablet, pill, capsule, powder, troche, solution, suppository, injection and the like. The agent may be formulated using a pharmaceutically acceptable excipient. Examples of the pharmaceutically acceptable excipient include lactose, sucrose, glucose, sorbitol, mannitol, potato starch, amylopectin, other various starches, cellulose derivatives (e.g., carboxymethyl cellulose, hydroxyethyl cellulose and the like), gelatin, magnesium stearate, polyvinyl alcohol, calcium stearate, polyethylene glycol wax, titanium dioxide, plant oils such as olive oil, peanut oil and sesame oil, paraffin oil, neutral fat base, ethanol, propylene glycol, physiological saline, sterilized water, glycerin, coloring agent, seasoning agent, concentrating agent, stabilizer, isotonic agent, buffering agent and other pharmaceutically acceptable excipients.

The agent of the present invention may contain the platinum complex of the present invention in the amount of 0.001–85% by weight, preferably 0.005–60% by weight.

Although the dosage of the agent varies mainly depending on the symptoms of the patient, it is 0.005–200 mg, preferably 0.01–50 mg for an adult per body weight per day.

The invention will now be described in more detail by way of examples.

EXAMPLE 1

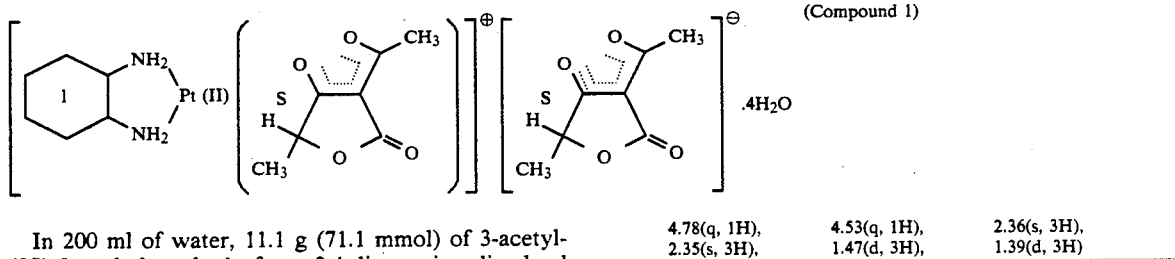

(Compound 1)

In 200 ml of water, 11.1 g (71.1 mmol) of 3-acetyl-(5S)-5-methyltetrahydrofuran-2,4-dione is dissolved and 500 ml (33.6 mmol) of aqueous solution of platinum (II) (trans-l-1,2-diaminocyclohexane) $(OH)_2$ is added dropwise thereto under cooling in ice. The resulting mixture is stirred at room temperature for 5 hours. Water is evaporated off by using a rotary evaporator and the resultant is evaporated to dryness under a reduced pressure using a vacuum pump. To the residue, 300 ml of tetrahydrofuran is added and the product attached to the inner wall of the container is pulverized. Powder is separated by filtration and the separated powder is washed with 100 ml of tetrahydrofuran and dried. The yield is 14.2 g. The resultant is dissolved in water and the resulting solution is subjected to liquid column chromatography containing styrene-divinylbenzene copolymer (MCI GEL CHP20P, commercially available from Mitsubishi Kasei Corporation) as the packing. The sample is developed with a solvent of 7:3 mixture of water/methanol. The factions containing the complex in high concentrations are combined and the combined solution was concentrated by using a rotary evaporator. The residue is crystallized by leaving the concentrate to stand in a refrigerator. The crystals are separated by filtration and the obtained crystals are further recrystallized twice from water. The yield after drying in air is 6.65 g (yield: 29%). The solubility in water is about 30 mg/ml.

The melting point, elementary analysis data and IR and NMR spectrum data are as follows:

Melting Point (Decomposition Point): ca.238° C.

| Elementary Analysis: As $C_{20}H_{36}N_2O_{12}Pt$ (tetrahydrate) | | | | |
|---|---|---|---|---|
| | C | H | N | Pt |
| Calcd. (%) | 34.74 | 5.25 | 4.05 | 28.21 |
| Found (%) | 34.75 | 5.20 | 4.05 | 28.22 |

IR $(KBr)(cm^{-1})$: 3346, 3170, 3082, 2938, 1750, 1651, 1603, 1562, 1543, 1493, 1460.

$^1$H NMR(400 MHz, in $D_2O$, internal standard is $^1$H in $D_2O$,

Measurement Temperature 60° C.) δ(ppm):

| 1,2-diaminocyclohexane moiety: | | |
|---|---|---|
| 2.60(m, 2H), | 2.13(d, 2H), | 1.64(m, 2H), |
| ca.1.39(2H), | 1.22(m, 2H) | |
| 3-acetyl-(5S)-5-methyltetrafuran-2,4-dione moiety; | | |
| 4.78(q, 1H), | 4.53(q, 1H), | 2.36(s, 3H), |
| 2.35(s, 3H), | 1.47(d, 3H), | 1.39(d, 3H) |

X-ray structural analysis of the crystals revealed that the obtained compound had the chemical structure of that of Compound 1.

To an aqueous solution containing 2 equivalents of 2-acetyl-(5S)-5-methyltetrahydrofuran-2,4-dione and one equivalent of barium hydroxide, an aqueous solution containing one equivalent of Pt(trans-l-1,2-diaminocyclohexane)$SO_4$ is added and the resulting mixture is stirred overnight. The generated precipitate of barium sulfate is removed by filtration. Water is removed from the filtrate by using a rotary evaporator and the resultant is evaporated to dryness under reduced pressure using a vacuum pump. Thereafter, by carrying out the same operation as in the above-described example, Compound 1 is also obtained.

EXAMPLE 2

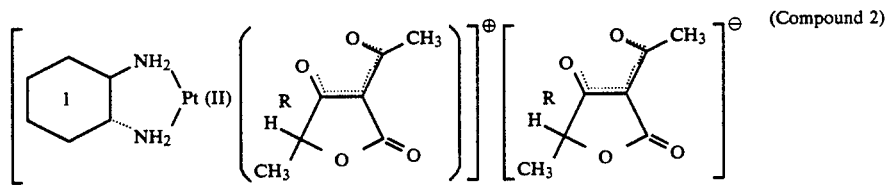

(Compound 2)

In 100 ml of water, 5.84 g (37.4 mmol) of 3-acetyl-(5R)-5-methyltetrahydrofuran-2,4-dione is dissolved and 278.5 ml (17.8 mmol) of an aqueous solution of Pt(II) (trans-l-1,2-diaminocyclohexane) $(OH)_2$ is added dropwise thereto. After stirring the resulting mixture overnight at room temperature, water is evaporated off by using a rotary evaporator and the resultant is evaporated to dryness under a reduced pressure using a vacuum pump. To the residue, 100 ml of tetrahydrofuran is added and the resultant is pulverized. The powder is separated by filtration and dried. The resulting powder is dissolved in water and the solution is subjected to liquid chromatography as in Example 1. The sample is developed with 7:3 mixture of water/methanol. The fractions containing the desired product are combined and the combined solution is concentrated by using a rotary evaporator. By leaving the concentrate to stand, crystals are precipitated. The crystals are recrystallized twice from water. The weight after drying in air is 1.65 g. The solubility in water is about 30 mg/ml.

The melting point, elementary analysis data and IR and NMR spectrum data are as follows:

Melting Point (Decomposition Point): ca.239° C.

| Elementary Analysis: as $C_{20}H_{28}N_2O_8Pt$ | | | | |
| --- | --- | --- | --- | --- |
|  | C | H | N | Pt |
| Calcd. (%) | 38.77 | 4.56 | 4.52 | 31.49 |
| Found (%) | 38.75 | 4.54 | 4.55 | 31.46 |

IR (KBr) (cm$^{-1}$): 3130, 3030, 2938, 1765, 1649, 1609, 1572, 1502, 1460, 1013.

$^1$H NMR(400 MHz, in D$_2$O, internal standard is $^1$H in D$_2$O,
Measurement Temperature 60° C.) δ(ppm):

| 1,2-diaminocyclohexane moiety: | | |
| --- | --- | --- |
| 2.60(m, 2H), | 2.13(d, 2H), | 1.64(m, 2H), |
| ca.1.38(2H), | 1.22(m, 2H) | |
| 3-acetyl-(5R)-5-methyltetrafuran-2,4-dione moiety: | | |
| 4.79(q, 1H), | 4.53(q, 1H), | 2.36(s, 3H), |
| 2.35(s, 3H), | 1.46(d, 3H), | 1.39(d, 3H) | umn containing MCI-GEL CHP20P. The developing solvent used was 7:3 mixture of water/methanol. The fractions containing the desired product are collected and concentrated by using a rotary evaporator. By leaving the resulting concentrate to stand, white precipitates are formed. The precipitates are collected by filtration and dried. The yield is 2.2 g. The solubility in water is about 33 mg/ml.

The melting point, elementary analysis data and IR and NMR spectrum data are as follows:Melting Point (Decomposition Point): 250°–254° C.

| Elementary Analysis: as $C_{20}H_{28}N_2O_8Pt$ | | | | |
| --- | --- | --- | --- | --- |
|  | C | H | N | Pt |
| Calcd. (%) | 38.77 | 4.56 | 4.52 | 31.49 |
| Found (%) | 38.68 | 4.42 | 4.47 | 31.51 |

IR (KBr)(cm$^{-1}$): 3062, 2932, 1756, 1647, 1609, 1566, 1502, 1460, 1330, 1238, 1089, 1067, 1029, 787, 661, 632, 590

$^1$H NMR(400 MHz, in D$_2$O internal Standard is $^1$H in D$_2$O, Room Temperature) δ(ppm):

| 1,2-diaminocyclohexane moiety: | | |
| --- | --- | --- |
| 1.20(m, 2H), | ca.1.4(2H), | 1.61(d, 2H), |
| 2.11(d, 2H), | 2.57(d, 2H) | |
| 3-acetyl-5-methyltetrafuran-2,4-dione moiety (Racemic): | | |
| 1.38(d, 3H), | 1.43(d, 1.5H), | 1.45(d, 1.5H), |
| 2.32(s, 3H), | 2.34(s, 3H), | 4.54(m, 1H), |
| 4.74(m, 1H) | | |

EXAMPLE 4

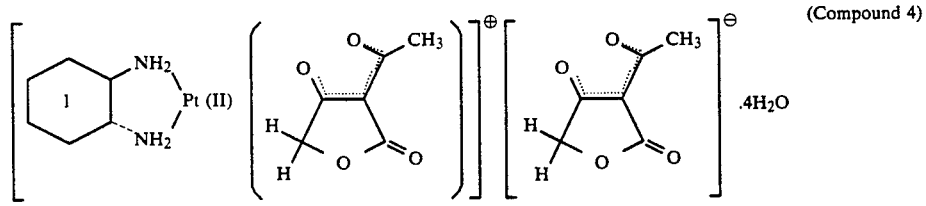

(Compound 4)

In 30 ml of water, 2.71 g (19 mmol) of 3-acetyltetrahydrofuran-2,4-dione is dissolved and the resulting

EXAMPLE 3

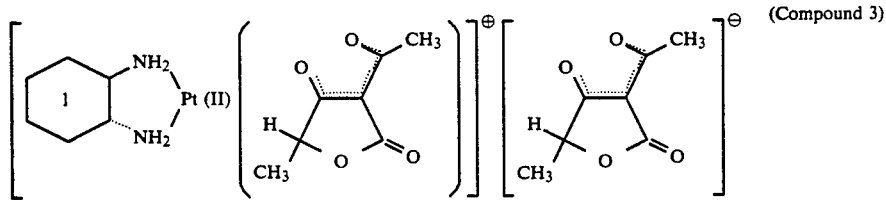

(Compound 3)

In 50 ml of water, 4.4 g (28.2 mmol) of racemic 3-acetyl-5-methyltetrahydrofuran-2,4-dione is dissolved and 190 ml (12.8 mmol) of an aqueous solution of Pt(II)(trans-l-1,2-diaminocyclohexane)(OH)$_2$ is added dropwise thereto. After stirring at room temperature for four hours, water is evaporated off by using a rotary evaporator and the resultant is evaporated to dryness under a reduced pressure using a vacuum pump. THF is added to the residue and the content is pulverized. Powder is separated by filtration and dried. The obtained powder is 4.3 g. The powder is dissolved in water and the solution is applied to liquid chromatography colsolution is cooled in ice. To the mixture, 135 ml (9 mmol) of aqueous solution of Pt(II)(trans-l-1,2-diaminocyclohexane) (OH$_2$) is added dropwise from a dropping funnel. The resulting mixture is left to stand overnight and the water is evaporated off by using a rotary evaporator. THF is added to the resultant and the content is pulverized. By collecting the powder by filtration and drying the powder, 4.09 g of yellow powder is obtained. The yellow powder is dissolved in water and the resulting solution is applied to liquid chromatography column containing MCI-GEL CHP20P. The developing solvent is 9:1 mixture of water/methanol. By concentrating the main fractions and leaving them to stand, crystals are precipitated. The crystals are collected by filtration and dried in air. The solubility in water is about 53 mg/ml.

The melting point, elementary analysis data and IR and NMR spectrum data are as follows:

Melting Point (Decomposition Point): 250° C.

| Elementary Analysis: as $C_{18}H_{32}N_2O_{12}Pt$ (tetrahydrate) | | | |
|---|---|---|---|
| C | H | N | Pt |
| Calcd. (%) 32.58 | 4.83 | 4.22 | 29.41 |
| Found (%) 32.56 | 4.82 | 4.26 | 29.50 |

IR (KBr)(cm$^{-1}$): 3390, 3162, 3076, 1752, 1649, 1605, 1497, 1460, 1056, 1025, 768, 702, 658

$^1$H NMR(400 MHz, in D$_2$O, internal standard is $^1$H in D$_2$O, Room Temperature) δ(ppm):

| 1,2-diaminocyclohexane moiety: | | |
|---|---|---|
| 1.03(m, 2H), | 1.21(m, 2H), | 1.45(d, 2H), |
| 1.93(d, 2H), | 2.40(m, 2H) | |
| 3-acetyltetrahydrofuran-2,4-dione moiety; | | |
| 2.15(s, 3H), | 2.17(s, 3H), | 4.23(s, 2H), |
| 4.33(s, 2H) | | |

3-acetyltetrahydrofuran-2,4-dione moitey; 2.15(s,3H), 2.17(s,3H), 4.23(s,2H), 4.33(s,2H)

EXAMPLE 5

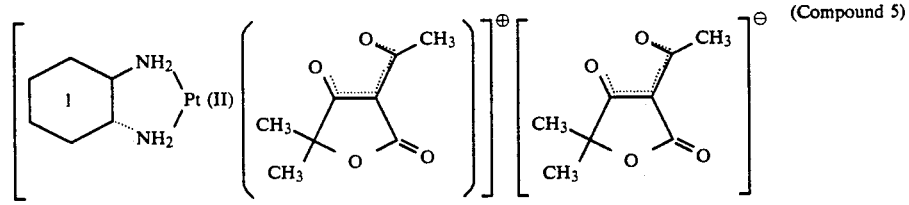

In 140 ml of ethanol, 3.57 g (21 mmol) of 3-acetyl-5,5-dimethyltetrahydrofuran-2,4-dione is dissolved and 148.8 ml (10 mmol) of an aqueous solution of Pt(II) (trans-l-1,2-diaminocyclohexane) (OH)$_2$ is added dropwise thereto. After leaving the resulting mixture to stand at room temperature overnight, the mixture is heated under stirring at 50°-60° C. for 2 hours. After evaporating off water from the reaction mixture by using a rotary evaporator, the resultant is further evaporated to dryness under reduced pressure using a vacuum pump. Ethyl acetate is added to the residue and the content is pulverized. Powder is collected by filtration and dried. Theuield is 4.47 g. The powder is dissolved in water and the resulting solution is applied to liquid chromatography column containing MCI-GEL CHP20P. The developing solvent used was 7:3 mixture of water/methanol. The fractions containing the product are collected and concentrated by a rotary evaporator. By adding THF to the concentrate, white powder is precipitated. The precipitates are collected by filtration and washed with THF. The resultant is dried under vacuum. The yield is 2.45 g (Compound 5).

The melting point, elementary analysis data and IR and NMR spectrum data are as follows:

Melting Point (Decomposition Point): 210°-215° C.

| Elementary Analysis: as $C_{22}H_{32}N_2O_8Pt$ | | | |
|---|---|---|---|
| | C | H | N | Pt |
| Calcd. (%) | 40.80 | 4.98 | 4.33 | 30.12 |
| Found (%) | 40.61 | 4.99 | 4.32 | 29.98 |

IR (KBr)(cm$^{-1}$): 3500, 3428, 3076, 2936, 1738, 1709, 1638, 1607, 1491, 1464, 1369, 1311, 1294, 1265, 1232, 1170, 1149, 1033, 961, 793, 658, 613.

$^1$H NMR(400 MHz, in D$_2$O, internal standard is $^1$H in D$_2$O) δ(ppm):

| 1,2-diaminocyclohexane moiety: | | |
|---|---|---|
| 1.20(m, 2H), | ca.1.4(2H), | 1.61(d, 2H), |
| 2.12(d, 2H), | 2.57(m, 2H) | |
| 3-acetyl-5,5-methyltetrahydrofuran-2,4-dione moiety; | | |
| 1.38(s, 3H), | 1.45(s, 3H), | 2.33(s, 3H), |
| 2.34(s, 3H) | | |

By recrystallizing the above-described complex from water, dihydrate of Compound 5 is obtained. Its solubility is 7 mg/ml.

Melting Point (Decomposition Point): ca.220° C.

(Compound 5)

| Elementary Analysis: as $C_{22}H_{36}N_2O_{10}Pt$ (dihydrate) | | | |
|---|---|---|---|
| | C | H | N | Pt |
| Calcd. (%) | 38.65 | 5.27 | 4.09 | 28.55 |
| Found (%) | 38.72 | 5.28 | 4.09 | 28.60 |

IR (KBr) (cm$^{-1}$): 3374, 3032, 2926, 1771, 1738, 1709, 1638, 1611, 1578, 1493, 1452, 1367, 1315, 1255, 1027, 961, 611

$^1$H NMR (400 MHz, in D$_2$O, internal standard is $^1$H in D$_2$O) δ(ppm):

The spectrum of the dihydrated complex is the same as that of non-hydrated complex.

EXAMPLE 6

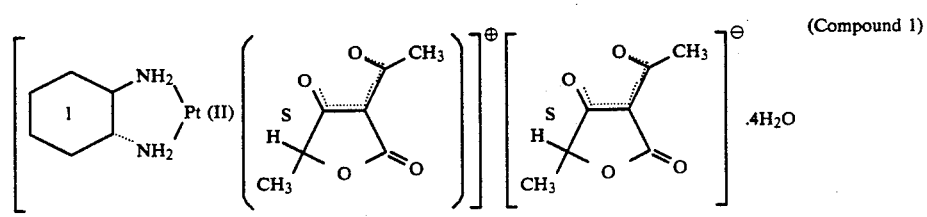

(Compound 1)

In 150 ml of water, 8.8 g(56.4 mmol) of 3-acetyl-(5S)-5-methyltetrahydrofuran-2,4-dione is dissolved and 335 ml (26.8 mmol) of an aqueous solution of Pt(II) (trans-l-1,2-diaminocyclohexane) (OH)$_2$ is added dropwise thereto under cooling in ice. The resulting mixture is stirred overnight at room temperature. Water is evaporated off from the mixture by using a rotary evaporator and the resultant was evaporated to dryness under reduced pressure using a vacuum pump. To the residue, 200 ml of tetrahydrofuran is added and the product attached to the inner wall of the container is pulverized. The powder is recovered by filtration and the obtained powder is washed with 50 ml of tetrahydrofuran and dried. To the obtained powder, 20 ml of water is added and the mixture is stirred. After cooling in ice, the formed precipitates are collected by filtration. To the obtained precipitates, 30 ml of water is added and the precipitates are dissolved by heating. By leaving the resultant in a refrigerator, crystals are precipitated. Recrystallization from water in the same manner is repeated. The formed crystals are dried in air. The yield is 3.61 g. By concentrating the mother liquor of the recrystallization, another 2.72 g of crystals are obtained. Elementary analysis and $^1$H NMR spectrum revealed that the obtained crystals are Compound 1.

EXAMPLE 7

In the abdominal cavities of CDF$_1$ mice (male, 6-week old, 5-10 mice/group, 10$^5$ mouse leukemia L1210 cells passaged in DBA/2 mice were transplanted. Defining the day of transplantation as Day 0, the compounds 1-5 of the present invention were separately administered intraperitoneally to mice on Day 1, Day 5 and Day 9, totaling 3 times. Each compound was administered after dissolving it in distilled water for injection. The evaluation of the anti-tumor activities of the platinum complexes against the L1210-transplanted mice was performed by T/C value which is obtained by the following equation:

$$T/C(\%) = \frac{\text{Average Survival Days of Treated Mice}}{\text{Average Survival Days of Control Mice}} \times 100$$

The results are shown in Table 1.

TABLE 1

Anti-tumor Activity in L1210-transplanted Mice

| Compound | Dose (mg/kg) | Survived Days (Mean ± Standard Deviation) | T/C (%) | Number of Survived Mice (Day 30) |
|---|---|---|---|---|
| Control Group | | 8.4 ± 0.5 | 100 | 0/10 |
| Compound 1 of the Invention | 3.1 | 10.8 ± 1.3 | 129 | 0/6 |
| | 6.3 | 11.5 ± 1.2 | 137 | 0/6 |
| | 12.5 | 11.7 ± 0.8 | 139 | 0/6 |
| | 25 | 13.8 ± 2.7 | 164 | 0/6 |
| | 50 | 12.8 ± 1.2 | 152 | 0/6 |
| | 100 | 9.8 ± 1.3 | 117 | 0/6 |
| Control Group | | 8.4 ± 0.5 | 100 | 0/10 |
| Compound 2 of the Invention | 3.1 | 10.7 ± 1.0 | 127 | 0/6 |
| | 6.3 | 11.7 ± 0.8 | 139 | 0/6 |
| | 12.5 | 16.0 ± 7.9 | 190 | 1/5 |
| | 25 | 15.3 ± 7.4 | 182 | 1/6 |
| | 50 | 15.0 ± 2.3 | 179 | 0/6 |
| | 100 | 11.3 ± 1.5 | 135 | 0/6 |
| Control Group | | 8.0 ± 1.6 | 100 | 0/10 |
| Compound 3 of the Invention | 1 | 9.3 ± 2.2 | 116 | 0/6 |
| | 5 | 10.2 ± 1.3 | 128 | 0/6 |
| | 10 | 15.0 ± 4.8 | 188 | 0/5 |
| | 25 | 12.0 ± 3.8 | 150 | 0/6 |
| | 50 | 12.8 ± 3.8 | 160 | 0/6 |
| | 100 | 10.0 ± 1.5 | 125 | 0/6 |
| Control Group | | 8.8 ± 1.2 | 100 | 0/10 |
| Compound 4 of the Invention | 3.1 | 12.5 ± 1.2 | 142 | 0/6 |
| | 6.3 | 13.8 ± 1.6 | 157 | 0/6 |
| | 12.5 | 14.0 ± 1.3 | 159 | 0/6 |
| | 25 | 15.0 ± 4.7 | 170 | 1/6 |
| | 50 | 6.2 ± 0.8 | 70 | 0/6 |
| Control Group | | 8.2 ± 0.6 | 100 | 0/10 |
| Compound 5 of the Invention | 1 | 8.5 ± 1.2 | 104 | 0/6 |
| | 10 | 9.3 ± 1.0 | 113 | 0/6 |
| | 25 | 11.4 ± 2.1 | 139 | 0/5 |
| | 50 | 11.4 ± 1.5 | 139 | 1/6 |
| | 100 | 13.5 ± 2.3 | 165 | 1/6 |

EXAMPLE 8

In the abdominal cavities of CDF$_1$ mice (male, 6-week old, 5-10 mice/group), 10$^5$ Cisplatin-resistant mouse leukemia L1210/CDDP cells passaged in DBA/2 mice were transplanted. Defining the day of transplantation as Day 0, the compounds of the present invention and control drugs were separately administered intraperitoneally to mice on Day 1, Day 5 and Day 9, totaling 3 times.

The compounds of the present invention and carboplatin were administered after dissolving them in distilled water for injection and cisplatin was used after dissolving it in physiological saline for injection. The effectiveness of the compounds was evaluated by using the T/C value as in Example 7. The results are shown in Table 2.

TABLE 2

Anti-tumor Activity in Cisplatin-resistant L1210-transplanted Mice

| Compound | Dose (mg/kg) | Survived Days (Mean ± Standard Deviation) | T/C (%) | Number of Survived Mice (Day 30) |
|---|---|---|---|---|
| Control Group | | 9.1 ± 0.7 | 100 | 0/10 |
| Compound 1 of the Invention | 3.2 | 10.8 ± 1.9 | 119 | 0/6 |
| | 6.3 | 10.5 ± 2.4 | 115 | 0/6 |
| | 12.5 | 16.2 ± 10.7 | 178 | 2/6 |
| | 25 | 20.3 ± 10.7 | 223 | 3/6 |
| | 50 | 13.8 ± 9.6 | 143 | 1/6 |
| | 100 | 8.0 ± 2.1 | 88 | 0/6 |
| Compound 4 of the Invention | 3.2 | 9.5 ± 1.2 | 104 | 0/6 |
| | 6.3 | 16.5 ± 8.5 | 181 | 1/6 |
| | 12.5 | 14.2 ± 8.0 | 156 | 1/6 |
| | 25 | 10.0 ± 2.6 | 110 | 0/6 |
| | 50 | 6.7 ± 1.6 | 74 | 0/6 |
| | 100 | 5.0 ± 2.8 | 55 | 0/6 |
| Cisplatin | 2.5 | 9.3 ± 1.0 | 102 | 0/6 |
| | 5 | 8.3 ± 0.5 | 91 | 0/6 |
| | 10 | 8.7 ± 0.8 | 96 | 0/6 |
| | 25 | 7.2 ± 1.6 | 79 | 0/6 |
| Carboplatin | 25 | 9.0 ± 1.1 | 99 | 0/6 |
| | 50 | 9.7 ± 0.8 | 107 | 0/6 |
| | 100 | 9.3 ± 0.8 | 102 | 0/6 |
| | 200 | 7.3 ± 1.5 | 80 | 0/6 |

EXAMPLE 9

Acute toxicity tests were performed on Compound 1 obtained in Example 1 and Compound 4 obtained in Example 4.

Each test drug was intraperitoneally administered to Slc:ICR mice (male, 5-week old, 6 mice/group). The test drug was used after dissolving in distilled water. From the death rate after 14 days from the administration, $LD_{50}$ value was calculated according Miller-Tainter method. The results are shown in Table 3.

TABLE 3

| Compound | $LD_{50}$ (mg/kg) |
|---|---|
| Compound 1 | 132 |
| Compound 4 | 52 |

Acute toxicity test in mice was performed n Compound 3 prepared in Example 3. $LD_{50}$ was determined in the same manner as described above except that the mice were 6-week old and 0.05% Tween 80 was used in place of distilled water for dissolving the compound. The $LD_{50}$ of this complex is 83 mg/kg.

REFERENCE EXAMPLE 1

[Pt(II)(trans-l-1,2-diaminocyclohexane)](3-acetyl-6-methyltetrahydropyran-2,4-dione)$_2$·H$_2$O (1) Synthesis of Complex According to EP337,459

In 100 ml (4.2 mmol) of an aqueous solution of [Pt(trans-l-1,2-diaminocyclohexane)(OH)$_2$], 1.72 g (10.1 mmol) of 3-acetyl-6-methyltetrahydropyran-2,4-dione was added and the resulting mixture was stirred at room temperature for 6 hours. Thereafter, the reaction mixture was concentrated to dryness at 45°–50° C. After washing the resulting solid with ethyl acetate, the resultant was dried under reduced pressure at 40°–45° C. to obtain 2.40 g (yield: 86%) of light yellow complex (Sample A).

The melting point, elementary analysis data and IR data of this complex are as follows:

Melting Point (Decomposition Point): 184°–188° C.

| Elementary Analysis: as $C_{22}H_{34}N_2O_9Pt$ | | | | |
|---|---|---|---|---|
| | C | H | N | Pt |
| Calcd. (%) | 39.70 | 5.15 | 4.21 | 29.31 |
| Found (%) | 39.3 | 4.9 | 4.3 | 28.0 |

IR (KBr)(cm$^{-1}$): 3420, 3200, 3080, 2980, 2940, 2860, 1700, 1660, 1620, 1570, 1390, 1290, 1260, 1060, 970, 770.

The above-described reaction was repeated twice and totaling 7.10 g of light yellow complex was obtained.

(2) Purification of Complex Obtained in (1)

To the light yellow complex obtained in (1), 200 ml of tetrahydrofuran is added and the resultant is stirred, followed by pulverization. The powder collected by filtration is washed with 100 ml of tetrahydrofuran. The filtrate is yellow. The obtained powder is dissolved in water and the resulting solution is passed through a column packed with MCI GEL CHP20P (commercially available from Mitsubishi Kasei Corporation) which is styrene-divinylbenzene copolymer. As the developing solvent, 7:3 mixture of water/methanol is used. Judging from liquid chromatogram, the fractions containing high concentration of complex are collected and combined, followed by concentration by using a rotary evaporator. The resulting concentrate is again subjected to the liquid column chromatography using the same column and the same developing solvent. The fractions containing high concentration of complex are collected and concentrated by a rotary evaporator. The resulting concentrate is evaporated to dryness using a lyophilizer. White powder in the amount of 2.64 g was obtained (Sample B).

The melting point, elementary analysis data and NMR spectrum data are as follows:

Melting Point (Decomposition Point): ca.230° C.

| Elementary Analysis: as $C_{22}H_{34}N_2O_9Pt$ | | | | |
|---|---|---|---|---|
| | C | H | N | Pt |
| Calcd. (%) | 39.70 | 5.15 | 4.21 | 29.31 |
| Found (%) | 39.42 | 4.91 | 4.15 | 29.1 |

$^1$H NMR(400 MHz, in D$_2$O, internal standard is $^1$H in D$_2$0) δ(ppm): 4.78(m,$^1$H), 4.48(m,1H), 2.6–2.3(m,8H), 2.29(s,3H), 2.23(s,3H,) 2.04(d,2H), 1.57(d,2H), 1.33(d,3H), 1.31(d,3H), 1.14(m,2H)

REFERENCE EXAMPLE 2

[Pt(II)(trans-l-1,2-diaminocyclohexane)](3-acetyltetrahydropyran-2,4-dione)$_2$.H$_2$O In 50 ml of ethanol, 1.56 g (10 mmol) of 3-acetyltetrahydropyran-2,4-dione was dissolved and 60 ml (4.0 mmol) of an aqueous solution of [Pt(trans-l-1,2-diaminocyclohexane)(OH)$_2$] solution was added thereto under stirring and cooling in ice. After leaving the resulting mixture to stand for 2 days at room temperature, the reaction mixture was concentrated under reduced pressure at 40° C. and dried. Tetrahydrofuran was added to the obtained solid and the resultant was pulverized and washed. After collecting the powder by filtration, the powder was dried under reduced pressure at room temperature to obtain 2.30 g of light yellow complex (yield: 90%). The light yellow complex was dissolved in water and purified by liquid chromatography in the same manner as in Reference Example 1(2) to obtain 0.75 g of white powder (Sample C).

The melting point, elementary analysis data and NMR spectrum data are as follows:

Melting Point (Decomposition Point): ca.240° C.

| Elementary Analysis: as C$_{20}$H$_{30}$N$_2$O$_9$Pt | | | |
|---|---|---|---|
| | C | H | N | Pt |
| Calcd. (%) | 37.68 | 4.74 | 4.39 | 30.60 |
| Found (%) | 37.44 | 4.56 | 4.40 | 30.9 |

$^1$H NMR(400 MHz, in D$_2$O, internal standard is $^1$H in D20) δ(ppm): 4.30(t,2H), 4.24(t,2H), 2.59(t,2H), 2.50–2.47(m,4H), 2.32(s,3H), 2.25(s,3H), 2.07(d,2H), 1.58(m,2H), 1.34(m,2H), 1.17(m,2H).

REFERENCE EXAMPLE 3

The Samples A, B and C synthesized in Reference Examples 1 and 2 were evaluated for their anti-tumor activities by the following method:

In the abdominal cavities of CDF$_1$mice (male, 6-week old, 6–10 mice/group), 105 mouse leukemia cells L1210 subcultured in DBA/2 mice were transplanted. Taking the day of transplantation as Day 0, the test drugs were separately administered intraperitoneally to the mice on Day 1, Day 5 and Day 9, totaling 3 times. Each drug was administered after dissolving or suspending it in 0.05% Tween 80 solution. The evaluation of the effectiveness was performed based on the T/C value which is obtained by the following equation as well as the number of survived mice on Day 30.

$$T/C(\%) = \frac{\text{Average Survival Days of Treated Mice}}{\text{Average Survival Days of Control Mice}} \times 100$$

The results are shown in Table 4.

TABLE 4

Anti-tumor Activity in L1210-transplanted Mice

| Compound | Dose (mg/kg) | Survived Days (Mean ± Standard Deviation) | T/C (%) | Number of Survived Mice (Day 30) |
|---|---|---|---|---|
| Control Group | | 8.4 ± 1.0 | 100 | 0/10 |
| Reference Example 1 Sample A | 1 | 8.5 ± 0.5 | 101 | 0/6 |
| | 10 | 11.5 ± 1.2 | 137 | 0/6 |
| | 25 | 14.2 ± 3.2 | 169 | 0/6 |
| | 50 | 17.0 ± 3.0 | 202 | 0/6 |
| | 100 | 15.5 ± 5.0 | 185 | 0/6 |
| | 200 | 6.0 | 71 | 0/6 |
| Control Group | | 8.4 ± 1.2 | 100 | 0/10 |
| Reference Example 1 Sample B | 25 | 8.5 ± 0.5 | 101 | 0/6 |
| | 50 | 8.8 ± 0.8 | 105 | 0/6 |
| | 100 | 9.2 ± 1.5 | 110 | 0/6 |
| | 200 | 9.5 ± 2.3 | 113 | 0/6 |
| Control Group | | 8.4 ± 1.0 | 100 | 0/6 |
| Reference Example 2 Sample C | 1 | 8.7 ± 0.8 | 104 | 0/6 |
| | 10 | 9.8 ± 1.6 | 117 | 0/6 |
| | 25 | 9.5 ± 0.5 | 113 | 0/6 |
| | 50 | 8.7 ± 2.2 | 104 | 0/6 |
| | 100 | 8.3 ± 0.8 | 99 | 0/6 |
| | 200 | 6.2 ± 1.5 | 74 | 0/6 |
| Control Group | | 8.4 ± 1.2 | 100 | 0/10 |
| Cisplatin | 2.5 | 13.0 ± 2.3 | 155 | 0/6 |
| | 5 | 13.8 ± 1.1 | 164 | 0/5 |
| | 7.5 | 18.3 ± 6.2 | 218 | 0/6 |

INDUSTRIAL APPLICABILITY

As described above, the platinum complex of the present invention has a solubility which enables intravenous administration and is stable in aqueous solutions. It is easy to purify by crystallization and the like. It has a strong anti-tumor activity and the toxicity is low. Thus, the platinum complex of the present invention is useful as an agent for treating malignant tumor.

We claim:

1. A platinum (II) complex represented by the following formula (A):

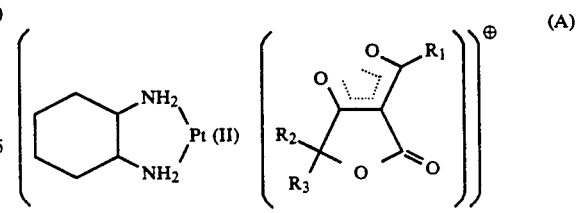

-continued

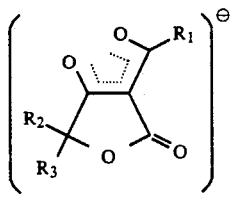

(wherein $R_1$ is a group containing 1-5 carbon atoms, $R_2$ and $R_3$ can be the same or different and are selected from the group consisting of hydrogen and a group containing 1-3 carbon atoms, the configuration of 1,2-diaminocyclohexane being cis, trans-l- or trans-d-).

2. The platinum (II) complex of claim 1, wherein $R_1$ is methyl.

3. The platinum (II) complex of claim 1 or 2, wherein $R_2$ and $R_3$ are hydrogen atom or methyl.

4. The platinum (II) complex of claim 3, wherein $R_2$ is hydrogen atom and $R_3$ is methyl.

5. A pharmaceutical composition for the treatment of malignant tumors comprising a therapeutically effective amount of the platinum complex represented by the general formula (A) of claim 1 and a pharmaceutically acceptable carrier therefor.

6. A platinum (II) complex represented by the following formula (A):

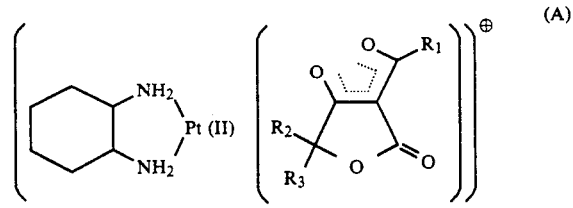

-continued

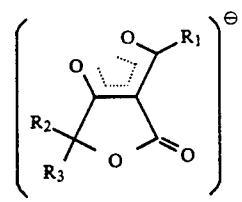

(wherein $R_1$ is $C_1$-$C_5$ alkyl or $C_1$-$C_5$ alkenyl, $R_2$ and $R_3$ can be the same or different and are selected from the group consisting of H, $C_1$-$C_3$, alkyl and $C_1$-$C_3$ alkenyl, the configuration of 1,2-diaminocyclohexane being cis, trans-l or trans-d-).

7. The pharmaceutical composition defined in claim 5 wherein $R_1$ is methyl.

8. The pharmaceutical composition defined in claim 5 wherein $R_2$ and $R_3$ are hydrogen or methyl.

9. The pharmaceutical composition defined in claim 5 wherein $R_2$ is hydrogen and $R_3$ is methyl.

10. A pharmaceutical composition for the treatment of leukemia comprising a therapeutically effective amount of the platinum complex represented by the general formula (A) of claim 1 and a pharmaceutically acceptable carrier therefor.

11. A pharmaceutical composition for the treatment of malignant tumors comprising a therapeutically effective amount of the platinum complex represented by the general formula (A) of claim 6 and a pharmaceutically acceptable carrier therefor.

12. A pharmaceutical composition suitable for administration to an animal having a tumor sensitive to the platinum complex defined in claim 1.

13. A pharmaceutical composition suitable for administration to an animal having a tumor sensitive to the platinum complex defined in claim 6.

* * * * *

UNITED STATES PATENT AND TRADEMARK OFFICE
CERTIFICATE OF CORRECTION

PATENT NO. : 5,302,587
DATED : April 12, 1994
INVENTOR(S) : Go Hata et al

Page 1 of 2

It is certified that error appears in the above-indentified patent and that said Letters Patent is hereby corrected as shown below:

In column 3, spanning lines 14-21, delete " 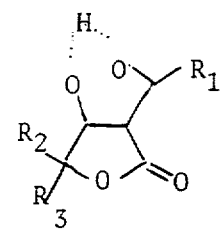 "

and substitute -- 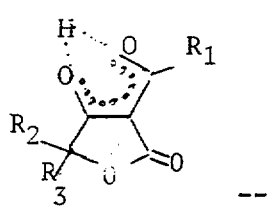 --

In column 5, spanning lines 21-31, delete

" 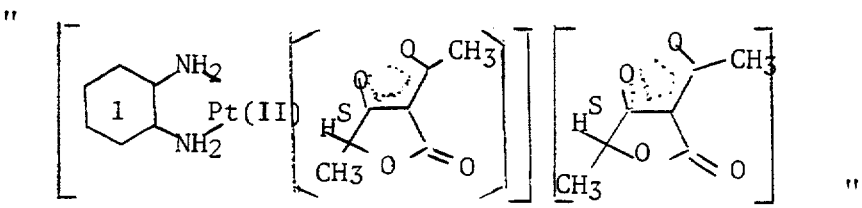 "

and substitute

-- 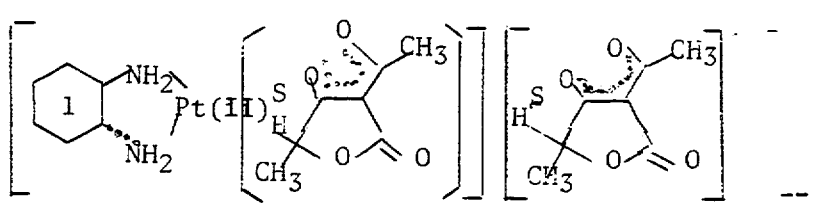 --

UNITED STATES PATENT AND TRADEMARK OFFICE
CERTIFICATE OF CORRECTION

PATENT NO. : 5,302,587
DATED : April 12, 1994
INVENTOR(S) : Go Hata et al

It is certified that error appears in the above-indentified patent and that said Letters Patent is hereby corrected as shown below:

In column 7, line 11, delete "1.65" and substitute --1.64--.

In column 15, line 68, delete "105" and substitute --$10^5$--.

Signed and Sealed this

Ninth Day of August, 1994

Attest:

BRUCE LEHMAN

Attesting Officer        Commissioner of Patents and Trademarks

UNITED STATES PATENT AND TRADEMARK OFFICE
CERTIFICATE OF CORRECTION

PATENT NO. : 5,302,587
DATED : April 12, 1994
INVENTOR(S) : Go Hata et al

It is certified that error appears in the above-indentified patent and that said Letters Patent is hereby corrected as shown below:

Column 3, spanning lines 1-8, delete

"
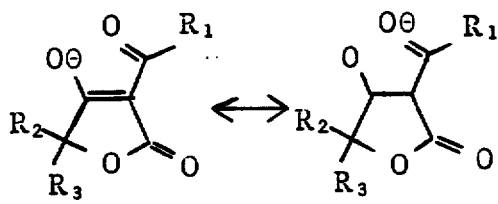
"

and substitute

--
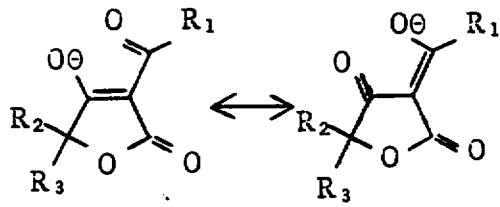
--

UNITED STATES PATENT AND TRADEMARK OFFICE
CERTIFICATE OF CORRECTION

PATENT NO. : 5,302,587
DATED : April 12, 1994
INVENTOR(S) : Go Hata et al

It is certified that error appears in the above-indentified patent and that said Letters Patent is hereby corrected as shown below:

Column 3, spanning lines 15-21, delete " 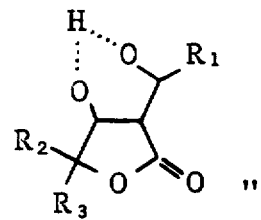

and substitute -- 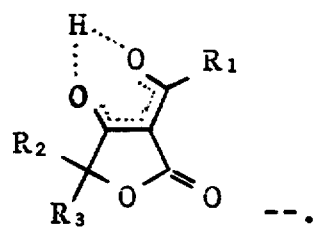 --.

Column 7, line 11, delete "1.65" and substitute --1.64--.
Column 11, line 66, delete "105" and substitute --$10^5$--.
Column 12, line 55, delete "105" and substitute --$10^5$--.
Column 15, line 68, delete "105" and substitute --$10^5$--.

UNITED STATES PATENT AND TRADEMARK OFFICE
CERTIFICATE OF CORRECTION

PATENT NO. : 5,302,587
DATED : April 12, 1994
INVENTOR(S) : Go Hata et al

It is certified that error appears in the above-indentified patent and that said Letters Patent is hereby corrected as shown below:

Column 5, spanning lines 21-31, delete

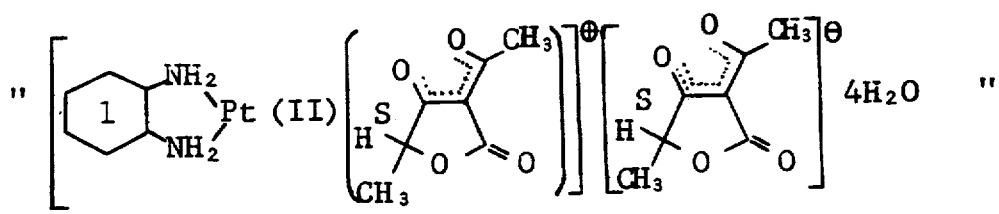

and substitute

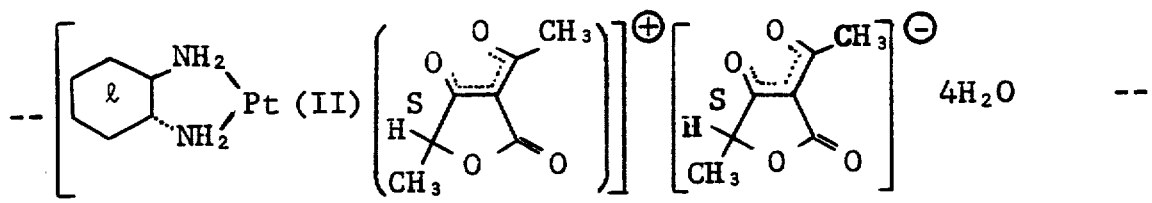

Signed and Sealed this

Twenty-seventh Day of September, 1994

Attest:

BRUCE LEHMAN

Attesting Officer   Commissioner of Patents and Trademarks